# United States Patent [19]
Wellington

[11] Patent Number: 4,472,680
[45] Date of Patent: Sep. 18, 1984

[54] CIRCUIT FOR PROCESSING ELECTRICAL SIGNALS GENERATED BY A CASING COLLAR INDICATOR INSTRUMENT

[75] Inventor: Charles H. Wellington, Houston, Tex.

[73] Assignee: Dresser Industries, Inc., Dallas, Tex.

[21] Appl. No.: 344,128

[22] Filed: Jan. 29, 1982

[51] Int. Cl.³ .............. G01N 27/82; G01R 33/12; G01R 19/165; H03K 5/22
[52] U.S. Cl. .................. 324/221; 307/234; 307/360; 324/140 R; 328/111
[58] Field of Search .............. 324/219-221, 324/103 P, 102, 111, 133, 140 R; 328/108, 111, 140, 146-149, 150; 307/234, 360, 362, 518, 519; 340/660-663

[56] References Cited
U.S. PATENT DOCUMENTS

| | | | |
|---|---|---|---|
| 2,967,994 | 1/1962 | Peterson | 324/221 |
| 3,434,046 | 3/1969 | Wilson et al. | 324/221 |
| 4,131,857 | 12/1978 | Clymer | 307/234 X |
| 4,162,453 | 7/1979 | Rudolph | 328/150 X |
| 4,208,627 | 6/1980 | Ebert | 324/133 X |
| 4,217,506 | 8/1980 | Sawyer et al. | 328/150 X |

FOREIGN PATENT DOCUMENTS
2402933 8/1974 Fed. Rep. of Germany ...... 324/133

OTHER PUBLICATIONS
Patent Application Ser. No. 963,875–Lichtenberg et al., Abstract.

Primary Examiner—Gerard R. Strecker
Attorney, Agent, or Firm—Patrick H. McCollum; Richard M. Byron

[57] ABSTRACT

An electrical signal representative of the detection of a mechanical coupling within a string of tubular goods is coupled into one input of each of a pair of parallel configured comparators. When the input signal level exceeds the value of complimentary reference levels the respective comparator generates an output signal. The composite output signal from the comparators is converted to a d.c. level which is compared to a fixed reference potential related to the duty cycle of a typical input signal. The comparator output signal is integrated and the peak value of which is stored by a peak detector. In the preferred embodiment the peak value is converted into digital form by an analog-to-digital converter.

9 Claims, 10 Drawing Figures

CIRCUIT FOR PROCESSING ELECTRICAL SIGNALS GENERATED BY A CASING COLLAR INDICATOR INSTRUMENT

BACKGROUND OF THE INVENTION

This invention relates generally to an apparatus for detecting coupling joints in subsurface tubing or casing set within a well bore and, more specifically, to electronic circuitry for processing electrical signals indicative of the coupling joints.

In the process of completing most oil and gas wells, a string of conduit or "casing" is placed into the earth borehole and cemented into place by pumping a slurry of cement between the borehole wall and the casing string. The casing is run into the borehole in various length sections with the diameter of the casing determined by the size at which the borehole is drilled. The sections of casing are joined into a string by a variety of threaded methods referred to generally as "collars".

Once casing is cemented into place within the borehole, the casing can be perforated at the suspected production zones as determined by commonly used well logging methods. When traversing the wellbore with a perforating instrument, it is desirable to have a quick, easy and reliable method to monitor the location of the perforating device in the borehole so that it can be aligned precisely opposite the formation to be perforated. To provide an accurate position determination, the operator must be able to correlate the depth of the perforating instrument with previously run well logs. This correlation is made easier by detecting when the instrument is proximate a specific casing collar. Such a determination is made using a casing collar indicating instrument.

Casing collar indicator instruments used in the industry typically emit a magnetic field by means of a permanent magnet or an oscillator circuit coupled to an electrical coil. Changes in the magnetic field resulting from variations in the casing mass caused by coupling joints are detected by the casing collar instrument and an electrical signal is transmitted to signal recovering circuitry in the form of either a shifting d.c. voltage signal or a sine wave signal of a predetermined frequency. Typically, the signal processing system had to have electronic circuitry for processing the d.c. signal and separate electronic circuitry for processing the a.c. signal. Further, the a.c. signal processing circuitry has been found to be less than fully reliable due to mistriggering. The most commonly used a.c. signal processing circuitry comprises a bandpass filter designed to pass the collar indicator instrument output frequency and attenuate other frequencies. It is not uncommon for this frequency dependent design to suffer from false triggering when a pulse repetition rate of approximately the same frequency as the collar indicator instrument sine wave signal is at the input or a large pulse at the input causes the bandpass filter to ring at its resonant frequency.

These and other disadvantages are overcome with the present invention by providing new and improved signal processing circuitry capable of handling either d.c. or a.c. collar indicator signals.

SUMMARY OF THE INVENTION

An input electrical signal representative of the detection of a casing joint is coupled into one input of each of a pair of comparators. The second input of one comparator is connected to a positive reference potential and the second input of the second comparator is connected to a complimentary negative reference potential. When the input signal value exceeds the value of the positive reference potential an output signal is generated by the first comparator and when the input signal value exceeds the value of the negative reference potential an output signal is generated by the second comparator. The composite output signal from the comparator pair is converted to a d.c. signal level by a d.c. converter, the output of which is coupled into a third comparator. This comparator generates an output signal the duration of which is dependent upon the relationship of the input d.c. level to a fixed reference value. The comparator output is coupled into an integrator circuit the output of which is a voltage proportional in value to the time duration of the comparator output signal. The integrator output voltage level is coupled into a peak detector circuit where the peak value of the integrator output is measured and coupled into an analog-to-digital convertor for conversion to a digital value which is coupled to an output terminal. After a predetermined amount of movement of the collar indicator instrument, an analog-to-digital conversion is made. A read of the analog-to-digital conversion, clears the peak detector for a new sample cycle.

DETAILED DESCRIPTION OF THE PREFERRED EMBODIMENT

Figure 1:
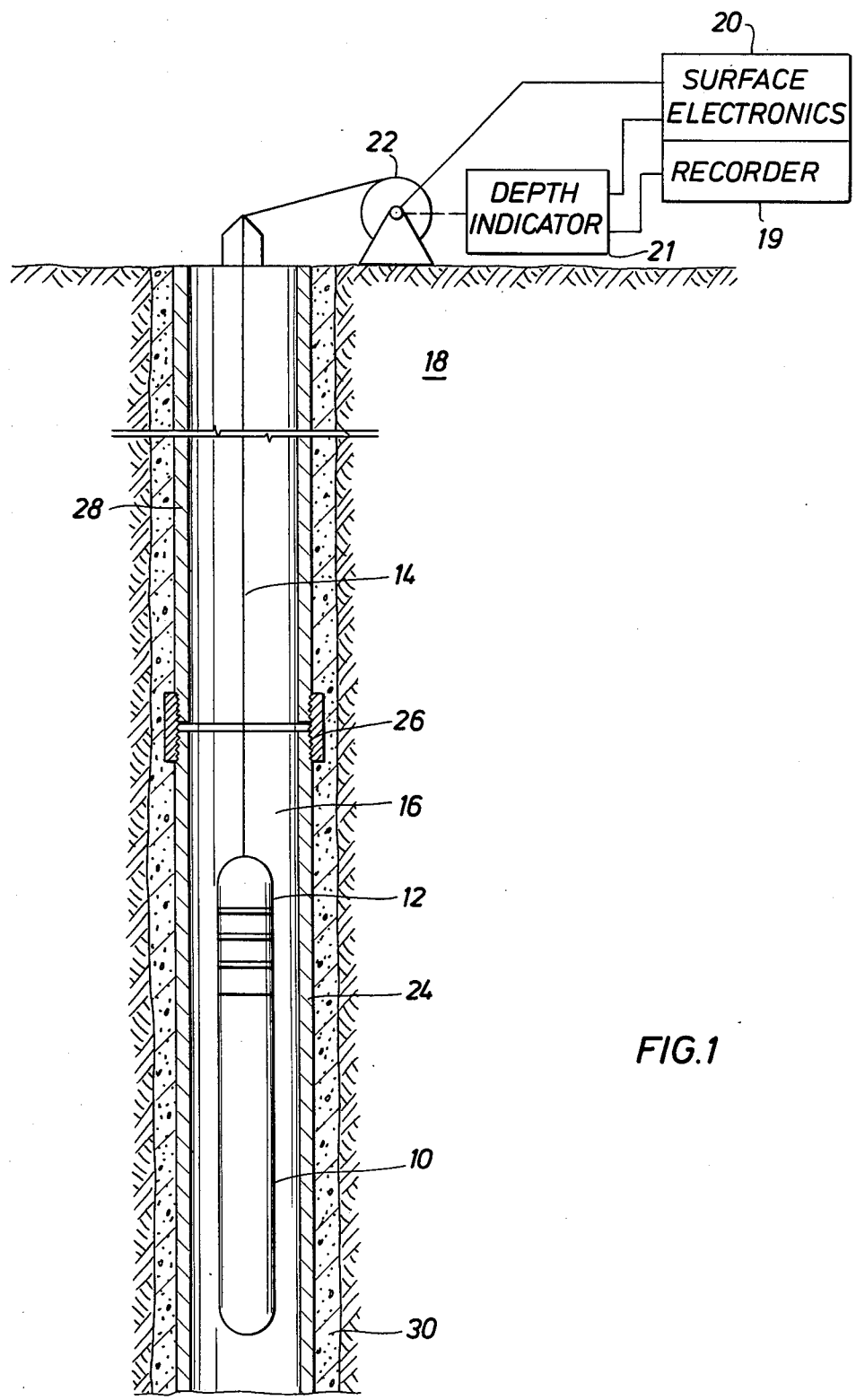
FIG. 1 is an overall schematic diagram of the well logging system of the present invention.

Referring now to the drawings in more detail, FIG. 1 illustrates a subsurface instrument 10, which may be a perforating gun or a well logging tool, with a casing collar indicator instrument 12 interconnected thereto. The instrument combination is suspended, by a means of an armor coated cable 14 within a borehole 16 penetrating the earth formations 18. The cable 14 is equipped with one or more electrical conductors which connect the subsurface instrumentation with the surface electronics 20. By winding or unwinding the cable 14 on a drum 22 located at the surface, the subsurface instrumentation is caused to traverse the borehole 16. The subsurface instrumentation is shown suspended within a length of casing 24 which is coupled by means of an external collar 26 to an additional casing section 28. The coupling of one casing joint to another is repeated over the length of the well forming a casing string which is cemented into place by pumping cement 30 into the annulus between the casing 24 and the earth formations 18. As further illustrated in FIG. 1, depth indicator 21 is connected to drum 22. Rotation of drum 22 in raising or lowering the subsurface instrument is converted into an electrical depth signal by depth indicator 21 and is coupled into a surface electronics 20 and recorder 19.

In the operation of the subsurface instrumentation of FIG. 1, as the instrument traverses the casing a magnetic field is emitted from collar indicator 12. As the collar indicator 12 comes proximate to a casing joint or mechanical coupling 26 the magnetic field is distorted. The distortion of the magnetic field is sensed by one or more receivers and an electrical signal is generated to indicate the presence of the casing joint. These casing joints provide permanent reference points which are correlated to depth and used to determine the locations of various instruments within the well and to correlate data obtained on various traversals of the well.

The casing collar indicator 12 illustrated in FIG. 1 will be typically either a so called "d.c." collar indicator or an "a.c." collar indicator. A d.c. collar indicator is one utilizing a permanent magnet to generate a fixed magnetic field within the casing. Changes in the magnetic field caused by the instrument passing a casing joint are detected by one or more receivers and a substantially d.c. output signal is generated. A typical d.c. collar indicator is more fully described in U.S. Pat. No. 2,967,994, issued to Glen Peterson, which is hereby incorporated by reference. The a.c. collar indicator is one utilizing a transmitter coil driven by an oscillator to generate a magnetic field within the casing. Changes in the casing mass, such as those caused by casing joints, distort the magnetic field resulting in an imbalance of the magnetic field detected by at least two receivers. The imbalance between the received signals results in the generation of an a.c. or sine wave output signal of a predetermined frequency indicating the presence of the casing joint. An apparatus suitable for use as an a.c. collar indicator is shown, for example, in U.S. patent application Ser. No. 963,875, by H. D. Lichtenberg et al, the disclosure of which is hereby incorporated by reference.

Figure 2:
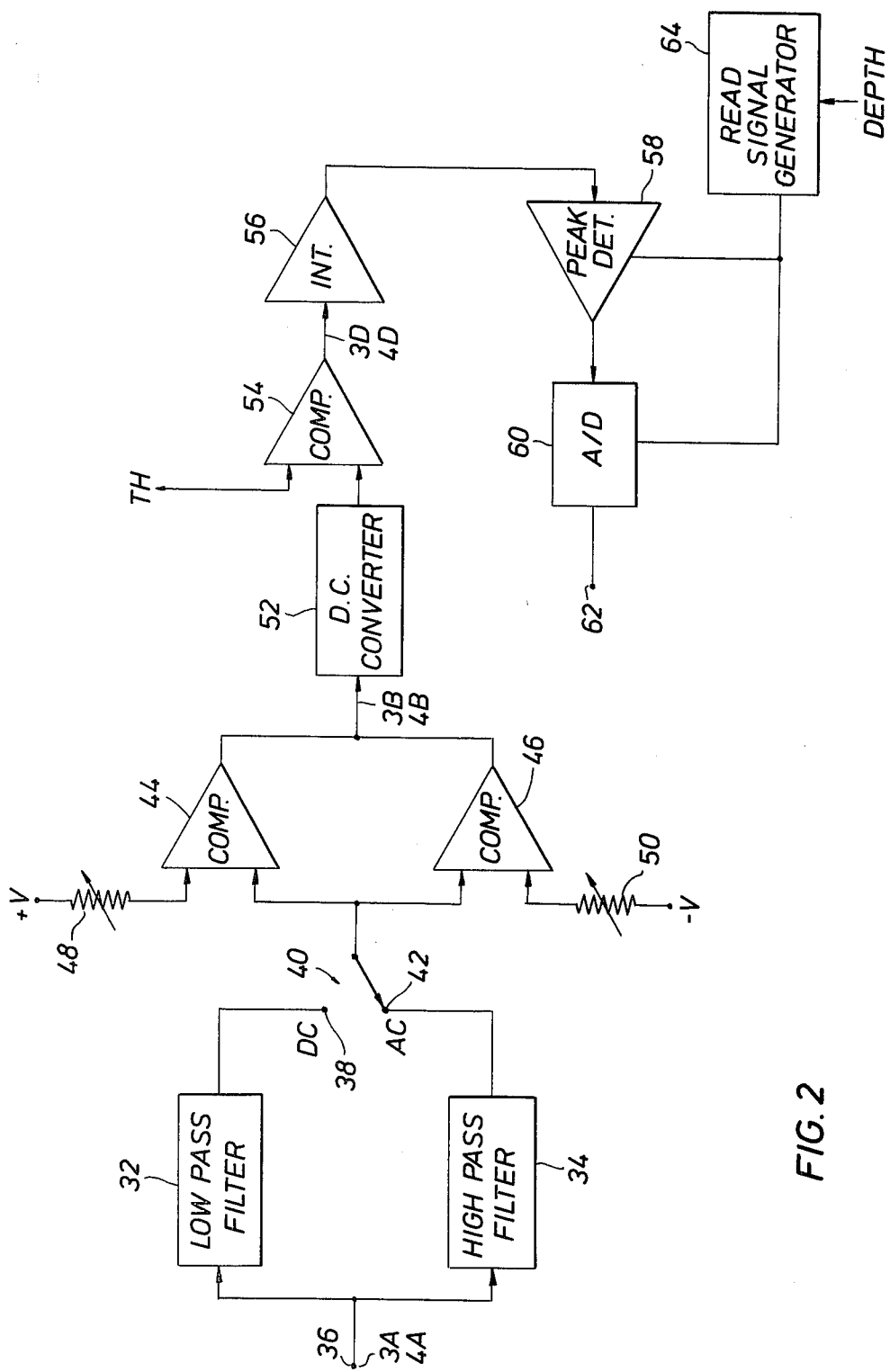
FIG. 2 is a schematic illustration of the signal processing circuitry according to the present invention.

Referring now to FIG. 2, there is illustrated the electronic signal processing circuitry of the present invention. The previously discussed casing collar indicator output electrical signal is coupled to low pass filter 32 and high pass filter 34 through input signal terminal 36. The output of low pass filter 32 is connected to contact 38 of electrical switch 40 while the output of high pass filter 34 is connected to contact 42 of electrical switch 40. The contact arm of electrical switch 40 is coupled simultaneously to one input of comparator 44 and comparator 46. The second input of comparator 44 is coupled through variable resistor 48 to a positive reference voltage source, +V. The second input of comparator 46 is coupled through variable resistor 50 to a negative reference voltage source, −V. The two variable resistors can be set by a control so the positive and negative thresholds move symetrically about ground.

The outputs of comparator 44 and comparator 46 are coupled simultaneously to the input of d.c. converter circuit 52 the output of which is coupled into one input of comparator 54. The second input of comparator is coupled to a fixed threshold voltage source, TH. The output of comparator 54 is coupled into the input of integrator circuit 56, the output of which is coupled into the input of peak detector circuit 58. The output of peak detector circuit 58 is coupled into the input of analog-to-digital convertor (A/D) 60, the output of which is coupled to signal output terminal 62. Peak detector circuit 58 and A/D 60 are also coupled to the ouput of read signal generator 64 the input of which is derived from a depth signal representative of instrument movement within the well bore.

Figure 3A:
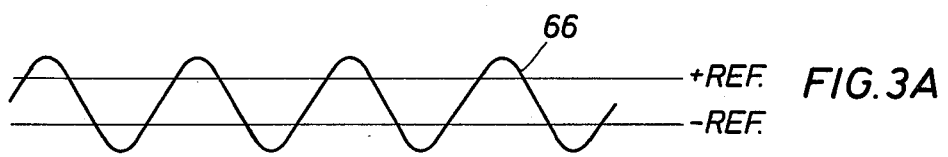
FIGS. 3A–3D are waveform diagrams of the electrical signals at various locations within the signal processing circuitry of FIG. 2 wherein an a.c. collar indicator is used in the well logging system of FIG. 1.
Figure 3B:

The operation of the electronic signal processing circuitry of FIG. 2 can be best explained when discussed with reference to FIGS. 3 and 4. The output electrical signal of the casing collar indicator instrument 12, illustrated by curves 66 and 68 of FIGS. 3A and 4A, respectively, is coupled to input signal terminal 36. The waveform display in FIG. 3A is representative of the output signal from a typical a.c. collar indicator instrument and is preferrably in the frequency range from between 1000 Hz and 3000 Hz. In the preferred embodiment of the present invention the output signal frequency of the collar indicator is at a frequency of approximately 2 kHz. The waveform display in FIG. 4A is representative of the output signal from a typical d.c. collar indicator instrument. While commonly referred to as d.c. output signal, in actuality the output signal frequency is in the range of 2 Hz to 3 Hz.

The electrical signal present at input terminal 36 when a casing collar is detected is simultaneously coupled to low pass filter 32 and high pass filter 34. Low pass filter 32 will pass low frequency input signals such as the output signal from a d.c. collar indicator instrument while blocking higher frequency input signals. High pass filter 34 has a pass band selected to pass input signals corresponding to the frequency of an a.c. collar indicator output. In the preferred embodiment, high pass filter 34 is selected to pass electrical signals in the 2 kHz frequency range.

Figure 4A:
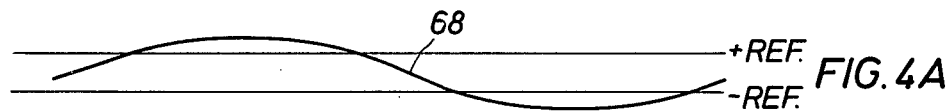
FIGS. 4A–4D are waveform diagrams of the electrical signals of various locations within the signal processing circuitry of FIG. 2 when a d.c. collar indicator is used in the well logging system of FIG. 1.
Figure 4B:
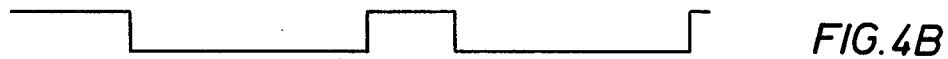

The output of low pass filter 32 is connected to one terminal 38 of selector switch 40 and the output of high pass filter 34 is connected to a second terminal 42 of selector switch 40. Selector switch 40 allows for mode selection depending upon the design of the collar indicator instrument. The selector arm of switch 40 is connected to one input of comparator 44 and comparator 46. The second input of comparator 44 is connected to a positive voltage source, +V, through variable resistor 48 and the second input of comparator 46 is connected to a negative voltage source, −V, through variable resistor 50. Resistors 48 and 50 are adjusted to establish a positive reference voltage potential, +REF, and a negative reference voltage potential, −REF, respectively. In the specific operation of the comparators 44 and 46, when the level of input signal 66 or 68 exceeds the value of the positive reference, comparator 44 will generate an output signal and when the level of the input signal 66 or 68 exceeds the value of negative reference, comparator 46 will generate an output signal. The composite output signal from comparators 44 and 46 is illustrated by FIGS. 3B and 4B. As illustrated, the outputs of comparators 44 and 46 are normally high and when the signal input of either comparator 44 or 46 exceeds the level of the reference potential the output of the respective comparator will go low until the value of the input signal returns to an absolute value level less than that of the reference potential. In the preferred embodiment of the present invention the input signal levels at comparators 44 and 46 are from between the range of approximately 300 mv to 1000 mv and the positive and negative reference levels are set to be approximately +50 mv and −50 mv, respectively.

Figure 3C:
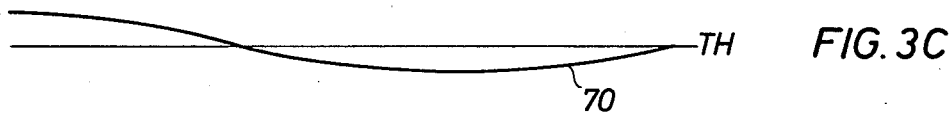
Figure 4C:
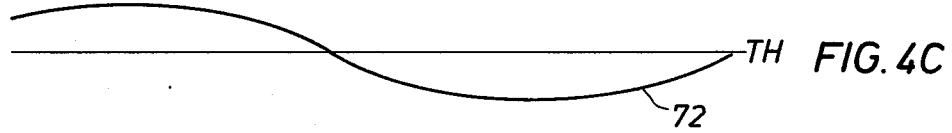

The output signal of comparators 44 and 46 is coupled to the input of d.c. converter circuit 52 where the pulse signal is converted to a d.c. signal level proportional to the pulse repetition rate as illustrated by curves 70 and 72 of FIGS. 3C and 4C, respectively. In effect, d.c. converter 52 converts the duty cycle of the input pulse signal to a d.c. level signal. The output of d.c.

converter is coupled into one input of comparator 54. The second input of comparator 54 is connected to a fixed voltage potential, TH. The value of the fixed voltage potential, TH, is selected to be approximately equal to the voltage the d.c. converter would generate for an input signal of approximately 66% duty cycle. When the value of the input signal 70 or 72 into comparator 54 becomes less than the value of TH, as illustrated in FIGS. 3C and 4C, comparator 54 generates an output signal the time duration of which is equal to the time that the value of the input signal is less than the value of the reference potential TH. The output signal from comparator 54 is illustrated in FIGS. 3D and 4D which show that the output of comparator 54 is normally low and goes high when the value of the input 72 is equal to the value of the fixed reference potential TH and remains high for the length of time the input 72 is less than TH.

Figure 3D:
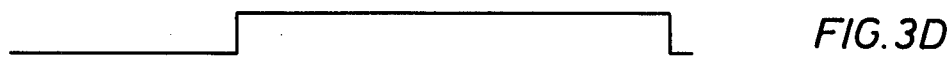
Figure 4D:
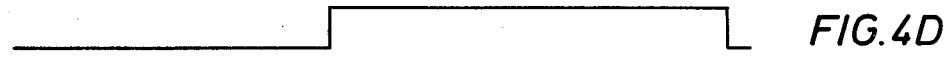

The output signal of comparator 54, FIG. 3D or 4D, is coupled into the input of integrator circuit 56 the output of which is a voltage level directly proportional to the time duration of the input signal. The output of integrator circuit 56 is coupled into the input of peak detector circuit 58. The output of peak detector circuit 58 approximates the true peak value of the input signal and is coupled into the input of analog-to-digital converter 60 where the analog peak value is converted upon receiving a command from the read signal generator 64 to a digital representation which is applied to output terminal 62. The peak analog value in the peak detector circuit 58 is cleared when a read pulse from the read signal generator has read the digital representation of the analog peak value. In the preferred operation of the circuitry of FIG. 2, peak detector circuit 58 is cleared in response to a read signal derived from instrument movement within the well bore as derived from depth indicator 21. More specifically, for every one-quarter of a foot of relative instrument movement within the borehole as derived from depth indicator 21, a read signal is generated which clears the peak detector circuit 58.

Thus, there has been described and illustrated herein apparatus in accordance with the present invention wherein new and improved casing collar indicator signal processing circuitry is described. However, while particular embodiments of the present invention have been illustrated and described, it will be apparent to those skilled in the art that changes and modifications may be made without departing from the invention in its broader aspects.

The embodiment of the invention in which an exclusive property or privilege is claimed are defined as follows:

1. A circuit for processing electrical signals generated by a casing collar indicator instrument traversing casing joints located in a string of tubular goods penetrating subsurface earth formations; comprising:
   first comparator means for comparing an input electrical signal generated by a casing collar indicator at the occurrence of a casing joint in a string of tubular goods to complementary positive and negative reference voltage levels and generating an electrical output pulse signal in response to the portion of said input electrical signal exceeding said reference voltage levels;
   converter means coupled to said first comparator means for producing a d.c. level shift output signal in response to said electrical output pulse signal from said first comparator means;
   second comparator means coupled to said converter means for comparaing said d.c. level shift signal to a predetermined reference voltage and generating an output pulse signal having a time duration dependent upon the relationship between said d.c. voltage level shift signal and said predetermined reference voltage;
   integrator means coupled to said second comparator means for integrating said output pulse signal of said second comparator means; and
   means coupled to said integrator means for generating a signal representative of the peak value of said integrator means output signal.

2. The apparatus of claim 1 further including filter means coupled to said first comparator means for passing said input electrical signal.

3. The apparatus of claim 2 wherein said filter means comprises a low pass filter.

4. The apparatus of claim 2 wherein said filter means comprises a band pass filter.

5. The apparatus of claim 1 wherein said first comparator means further comprises:
   a first comparator circuit having first and second inputs, said first input coupled to said positive reference level; and
   a second comparator circuit having first and second inputs, said first input coupled to said negative reference level and said second input and the output connected in parallel with said first comparator circuit.

6. The apparatus of claim 5 wherein said positive and negative references voltage levels are symetrical.

7. The apparatus of claim 1 wherein said predetermined reference potential is functionally related to the duty cycle of a typical input electrical signal.

8. The apparatus of claim 1 further including means for converting said peak value signal representation to digital format.

9. The apparatus of claim 8 further including means responsive to said instrument traversal of said tubular goods for generating an electrical signal to clear said peak value signal generating means.

* * * * *